US005699795A

United States Patent [19]
Richards-Kortum et al.

[11] Patent Number: 5,699,795
[45] Date of Patent: Dec. 23, 1997

[54] OPTICAL PROBE FOR THE DETECTION OF CERVICAL NEOPLASIA USING FLUORESCENCE SPECTROSCOPY AND APPARATUS INCORPORATING SAME

[75] Inventors: Rebecca Richards-Kortum; Costas Pitris, both of Austin; Michele Follen Mitchell, Houston, all of Tex.

[73] Assignee: Board of Regents, The University of Texas System, Austin, Tex.

[21] Appl. No.: 415,356

[22] Filed: Mar. 31, 1995

[51] Int. Cl.$^6$ .................................................. A61B 6/00
[52] U.S. Cl. ....................................................... 128/634
[58] Field of Search .................................. 128/664, 665, 128/633, 634; 250/461.2

[56] References Cited

U.S. PATENT DOCUMENTS

| | | | |
|---|---|---|---|
| 4,786,813 | 11/1988 | Svanberg et al. | 250/461.1 |
| 4,930,516 | 6/1990 | Alfano et al. | |
| 5,042,494 | 8/1991 | Alfano | 128/665 |
| 5,046,501 | 9/1991 | Crilly | 128/665 |
| 5,115,137 | 5/1992 | Andersson-Engels et al. | 250/461.2 |
| 5,125,404 | 6/1992 | Kittrell | 128/634 |
| 5,131,398 | 7/1992 | Alfano et al. | 128/665 |
| 5,168,162 | 12/1992 | Oong et al. | 250/339 |
| 5,174,297 | 12/1992 | Dalkuzono | 128/665 |
| 5,201,318 | 4/1993 | Rava et al. | 128/665 |
| 5,261,410 | 11/1993 | Alfano et al. | 128/664 |
| 5,303,026 | 4/1994 | Strobl et al. | 356/318 |
| 5,318,024 | 6/1994 | Kittrell et al. | 128/634 |
| 5,348,018 | 9/1994 | Alfano et al. | 128/65 |
| 5,361,759 | 10/1995 | Genevier et al. | 128/634 |
| 5,408,996 | 4/1995 | Salb | 128/633 |
| 5,421,339 | 6/1995 | Ramanujam et al. | 128/665 |

OTHER PUBLICATIONS

K. Schomacker et al., "Ultraviolet Laser-Induced Fluorescence of Colonic Tissue: Basic Biology and Diagnostic Potential," *Lasers in Surgery and Medicine*, 12:63–78, 1992.

R. Cothren et al., "Gastrointestinal Tissue Diagnosis by Laser-Induced Fluorescence Spectroscopy at Endoscopy," *Gastrointestinal Endoscopy*, 36:105–111, 1990.

S. Andersson-Engels et al., "Fluorescence Imaging and Points Measurements of Tissue: Appliations to the Demarcation of Malignant Tumors and Atherosclerotic Lesions from Normal Tissue," *Photochemistry and Photobiology*, 53:807–814, 1991.

R. Rava et al., "Early Detection of Dysplasia in Colon and Bladder Tissue Using Laser-Induced Fluorescence," *SPIE, Optical Methods for Tumor Treatment and Early Diagnosis: Mechanisms and Techniques*, 1426:68–78, 1991.

(List continued on next page.)

*Primary Examiner*—Scott Getzow
*Attorney, Agent, or Firm*—Arnold, White & Durkee

[57] ABSTRACT

A probe, and an apparatus incorporating the probe, for detecting tissue abnormality, particularly precancerous cervical tissue, through fluorescence spectroscopy are disclosed. In vivo fluorescence excitation and detection can be accomplished easily and accurately using a probe whose tip conforms to the surface of the cervix. In addition, a higher number of fiber pairs provides more information and, therefore, more accurate diagnosis.

21 Claims, 8 Drawing Sheets

OTHER PUBLICATIONS

R. Cothren et al., "Argon Ion Laser–Induced Tissue Fluorescence: Clinical Spectroscopic Studies," *SPIE, Optical Fibers in Medicine III*, vol. 906, Abstract only, 1988.

S. Lam et al., "Detection of Dysplasia and Carcinoma *In Situ* by Ratio Fluorometry," *Am. Rev. Respir. Dis.*, 146:1458–1461, 1992.

R.R. Alfano et al., "Optical Spectroscopic Diagnosis of Cancer in Normal Breast Tissue," *J. Opt. Soc.Am. B.*, 6:1015–1023, May 1989.

R.R. Alfano et al., "Fluorescence Spectra from Cancerous and Normal Human Breast and Lung Tissues," *IEEE Journal of Quantum Electronics*, QE–23:1806–1811, Oct. 1987.

J. Hung et al., "Autofluorescence of Normal and Malignant Bronchial Tissue," *Lasers in Surgery and Medicine*, 11:99–105, 1991.

R. Richards–Kortum et al., "Spectroscopic Diagnosis of Colonic Dysplasia," *Photochemistry and Photobiology*, 53:777–786, 1991.

C. Kapadia et al., "Laser–Induced Spectroscopy of Human Colonic Mucosa: Detection of Adenomatous Transformation," *Gastroenterology*, 99:150–157, 1990.

P. Wong et al., "Infrared Spectroscopy of Exfoliated Human Cervical Cells: Evidence of Extensive Structural Changes During Carcinogensis," *Proc. Natl. Acad. Sci. USA*, 88:10988–10992, 1991.

W. Glassman, "Ultraviolet Excited Fluorescent Spectra from Non–Malignant and Malignant Tissues of the Gynecological Tract," *Lasers in the Lifesciences*, 49–58, 1992.

W. Lohmann et al., "Native Fluorescence of the Cervix Uteri as a Marker for Dysplasia and Invasive Carcinoma," *European Journal of Obstetrics & Gynecology and Reproductive Biology*, 31:249–253, 1989.

N. Ramanujam et al., "Diagnosis of Cervical Intraepithelial Neoplasia Using Laser–Induced Fluorescence," *Poster Presentation at Future Directions of Lasers in Surgery and Medicine III*, 1993.

R. Walpole and R. Myers, *Tests of Hypotheses, In: Probability and Statistics for Engineers and Scientists*, 2nd Ed., Chapter 7:v, 238–259, 1978.

W. Dillon and M. Goldstein, *Principal Components Analysis, In: Multivariate Analysis, Methods and Applications*, Chapter 2:23–392, 1984.

C. Liu et al., "Raman, Fluorescence, and Time–Resolved Light Scattering as Optical Diagnostic Techniques to Separate Diseased and Normal Biomedical Media," *J Photochem. Photobiol. B*: Biol., 16:187–209, 1992.

D. Redd et al., "Raman Spectroscopic Characterization of Human Breast Tissues: Implications for Breast Cancer Diagnosis," *Applied Spectroscopy*, 47(6):787–791, 1993.

R. Alfano et al., "Human Breast Tissues Studied by IR Fourier Transform Raman Spectroscopy," *Lasers in the Life Sciences*, 4(1):23–28, 1991.

G. Small et al., "Strategies for Coupling Digital Filtering with Partial Least–Squares Regression: Application to the Determinationof Glucose in Plasma by Fourier Transform Near–Infrared Spectroscopy," *Anal. Chem.*, 65:3279–3289, 1993.

OPTICAL PROBE FOR THE DETECTION OF CERVICAL NEOPLASIA USING FLUORESCENCE SPECTROSCOPY AND APPARATUS INCORPORATING SAME

BACKGROUND OF THE INVENTION

The field of the invention relates to optical probes used for the screening and diagnosis of tissue abnormalities, and apparatus incorporating such probes. In particular, the invention relates to fluorescent spectroscopy probes and apparatus to detect cancerous and precancerous tissues of the cervix.

Cervical cancer is the second most common malignancy in women worldwide, exceeded only by breast cancer and in the United States, it is the third most common neoplasm of the female genital tract—15,000 new cases of invasive cervical cancer and 55,000 cases of carcinoma in situ (CIS) were reported in the U.S. in 1994. In 1994, an estimated 4,600 deaths occurred in the United States alone from cervical cancer. However, in recent years, the incidence of pre-invasive squamous carcinoma of the cervix has risen dramatically, especially among young women. Women under the age of 35 years account for up to 24.5% of patients with invasive cervical cancer, and the incidence is continuing to increase for women in this age group. It has been estimated that the mortality of cervical cancer may rise by 20% in the next decade unless further improvements are made in detection techniques.

The mortality associated with cervical cancer can be reduced if this disease is detected at the early stages of development or at the pre-cancerous state (cervical intraepithelial neoplasia (CIN)). A Pap smear is used to screen for CIN and cervical cancer in the general female population. This technique has a false-negative error rate of 15–40%. An abnormal Pap smear is followed by colposcopic examination, biopsy and histologic confirmation of the clinical diagnosis. Colposcopy requires extensive training and its accuracy for diagnosis is variable and limited even in expert hands. A diagnostic method that could improve the performance of colposcopy in the hands of less experienced practitioners, eliminate the need for multiple biopsies and allow more effective wide scale diagnosis could potentially reduce the mortality associated with cervical cancer.

Recently, fluorescence, infrared absorption and Raman spectroscopies have been proposed for cancer and precancer diagnosis. Many groups have successfully demonstrated their use in various organ systems. Auto- and dye-induced fluorescence have shown promise in recognizing atherosclerosis and various types of cancers and precancers. Many groups have demonstrated that autofluorescence may be used for differentiation of normal and abnormal tissues in the human breast and lung, bronchus and gastrointestinal tract. Fluorescence spectroscopic techniques have also been investigated for improved detection of cervical dysplasia.

Despite these advances, there remains a need for diagnostic tools with improved accuracy and ease of use. Such methods will permit more early diagnosis, more effective patient management and, potentially, reduce mortality.

SUMMARY OF THE INVENTION

Thus, it is an objective of the present invention to provide improved tools for the early detection of neoplasia. In particular, it is an objective of the present invention to provide improved spectroscopic probes for the identification of abnormal cervical tissue, thereby providing a rapid, accurate and simple method for detecting neoplastic cervical tissue. It is another objective of the present invention to provide an improved apparatus incorporating the improved probes for the identification of abnormal cervical tissue.

In satisfying these and other objectives, there is provided a probe for the optical diagnosis of tissue abnormalities at the cervix, and an apparatus incorporating the probe. In one embodiment, the present invention provides for the detection of tissue abnormality in a tissue sample in vivo by illuminating a cervical surface sample with a series of electromagnetic radiation wavelengths. Also provided are means to measure the fluorescence intensity spectra emitted from the tissue as a result of illumination with the electromagnetic radiation.

An optical probe for cervical examination is provided comprising (a) a probe casing having an elongate portion and at least two openings, wherein one of said openings is disposed at a distal tip of said elongate portion of said casing; (b) a plurality of optical fiber pairs, each of said pairs comprising an excitation fiber and a collection fibers, said optical fibers entering said casing at the non-tip opening and traversing said casing to said tip opening; and (c) an optically transparent window with a surface structured to conform to the surface of the human cervix, said window covering said tip opening.

In an exemplary embodiment, the probe window is substantially conical. In another embodiment, the number of fiber pairs is 31 or 357. In yet another embodiment, the window is comprised of quartz or BK7 glass.

These and other features and advantages of the present invention will become apparent to those of ordinary skill in this art with reference to the appended drawings and following detailed description.

DETAILED DESCRIPTION

I. Introduction

Clinical detection of neoplasias can be divided into two different kinds of analysis. First, screening provides a way to identify suspicious samples taken from a rather large pool of subjects. Subjects may be from the population as whole or they may be part of a group identified as having a higher than average risk for one or more neoplasms. It is desirable that, because of the sheer number of tests, screening assays be relatively rapid, easy to conduct and inexpensive. It also is essential that the exhibit a low false-negative rate.

Once patients have been screened, it is necessary to proceed with more detailed testing that can be referred to generically as diagnosis. In diagnosis, the neoplastic nature of the sample is confirmed and, in addition, further information on the type and degree of dysplasia is obtained. This provides the clinician with an understanding of the disease state necessary to begin a treatment regimen. For diagnosis, cost, ease of application and rapidity are less important, though always desirable. It is important, however, that diagnostic procedures be accurate with respect to the kind of neoplasm identified and its clinical stage.

The present invention permits accurate measurements for the second kind of detection, diagnosis. Present probe technology is limited by both the number of fibers that can be concentrated at the probe tip, both for excitation and detection purposes. In addition, the non-conforming shape of prior art probe tips precludes accurate fluorescent measurements. It is believed that by using a more fibers and a probe tip that conforms to the surface of the cervix, the accuracy of fluorescent measurements can be improved. In addition, the possibility for automation has further benefits in terms of time and expense.

A. Probe Design

The probe of the present invention is designed primarily for use in the vaginal cavity but can, in theory, be used in other situations including oral, rectal and intraoperative procedures. Regardless, the probe will comprise at least a portion that is elongated and suitable for insertion into any of the aforementioned body cavities or into a surgical field. The elongation is formed from the housing of the probe. The housing preferably is rigid but, in some circumstances, may be flexible. Regardless of the rigidity, the housing must provide sufficient protection for optical fibers disposed therein. The housing also should be durable in that it can withstand harsh chemical treatment, i.e., chemical sterilization and disinfection. Typical materials include various plastics, metals, resins, polymers, and the like. Preferred housing materials are carbonized (black) epoxy and aluminum. Further, the housing may be encased in a protective coating such as heat-shrink tubing.

The housing also will comprise at least two openings, the first of which permits entry fiber optic bundles. In addition, the housing comprises a cavity connecting the two openings. Thus, the fiber optic bundles pass though the first opening, traverse the cavity and are present at the second opening. The bundles are comprised of fiber pairs, comprising excitation and detection fibers. The fibers typically are comprised of a central core and a cladding surrounding the core. Any optical fiber can be employed in the disclosed probe and those of skill in the art are able to select fibers having varying properties depending on the particular use envisioned.

Figure 1A:
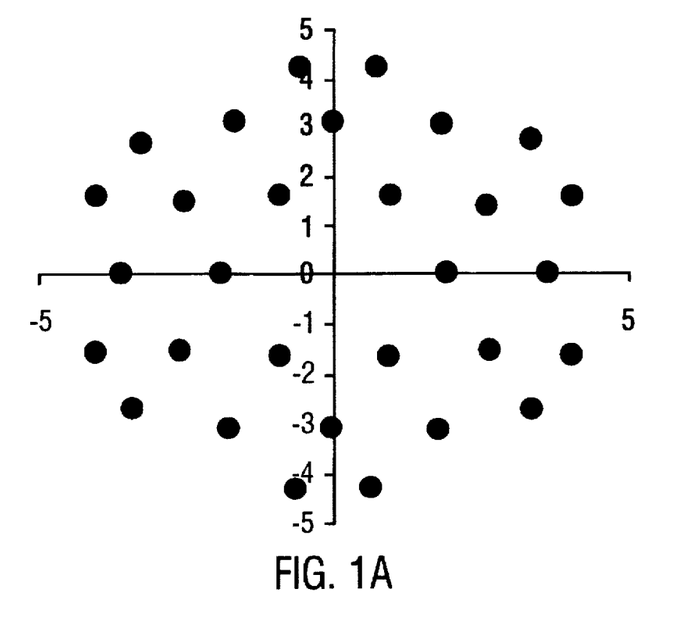
FIG. 1A shows the cartesian coordinates for a 31 fiber pair probe tip configuration, in accordance with an embodiment of the present invention.
Figure 1B:
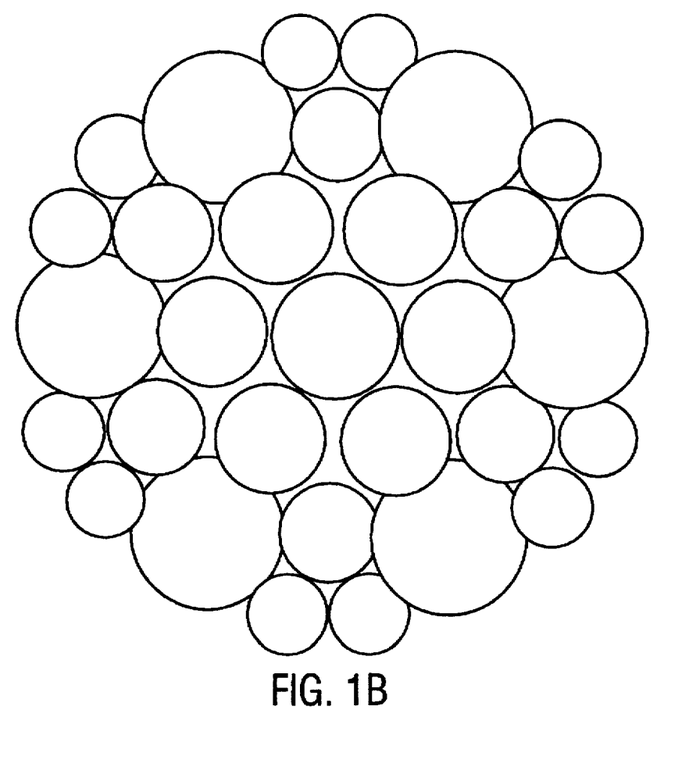
FIG. 1B shows the actual distribution for the 31 fiber pair probe tip configuration of FIG. 1.
Figure 2:
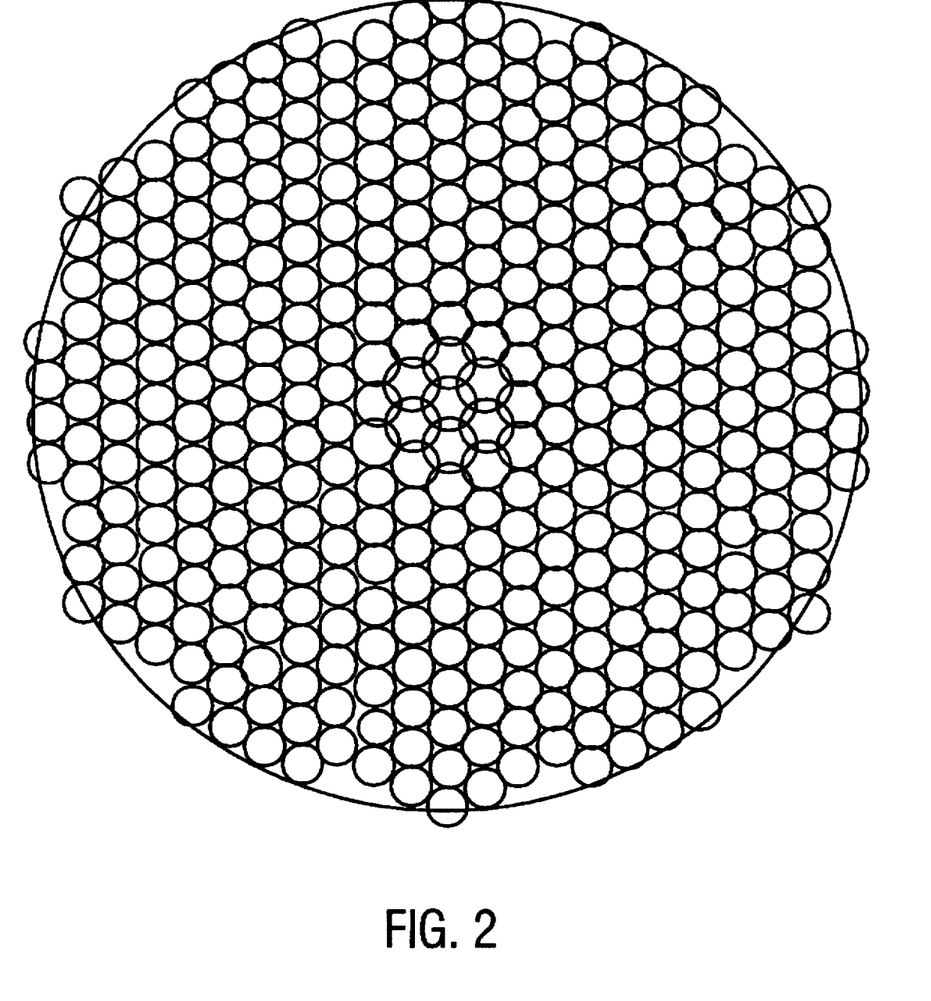
FIG. 2 shows the actual distribution for a 357 fiber pair probe tip configuration, in accordance with another embodiment of the present invention.

The disposition of fibers at the second opening is an important aspect of the present invention. In an exemplary embodiment, 31 fiber pairs are arranged as shown in FIG. 1B. In another exemplary embodiment, 357 fiber pairs are arranged as shown in FIG. 2. It is desirable that as large a number of fiber pairs as possible be used; the more fiber pairs, the more information provided by the probe. There is a point of diminishing returns, however, when crowding of the fibers causes cross-talk. To a certain extent, cross-talk can be reduced by altering the signal energy and by altering the timing of the detection. Again, those of skill in the art will be able to select these parameters, based on the particular endeavor and the fiber configuration.

Figure 5:
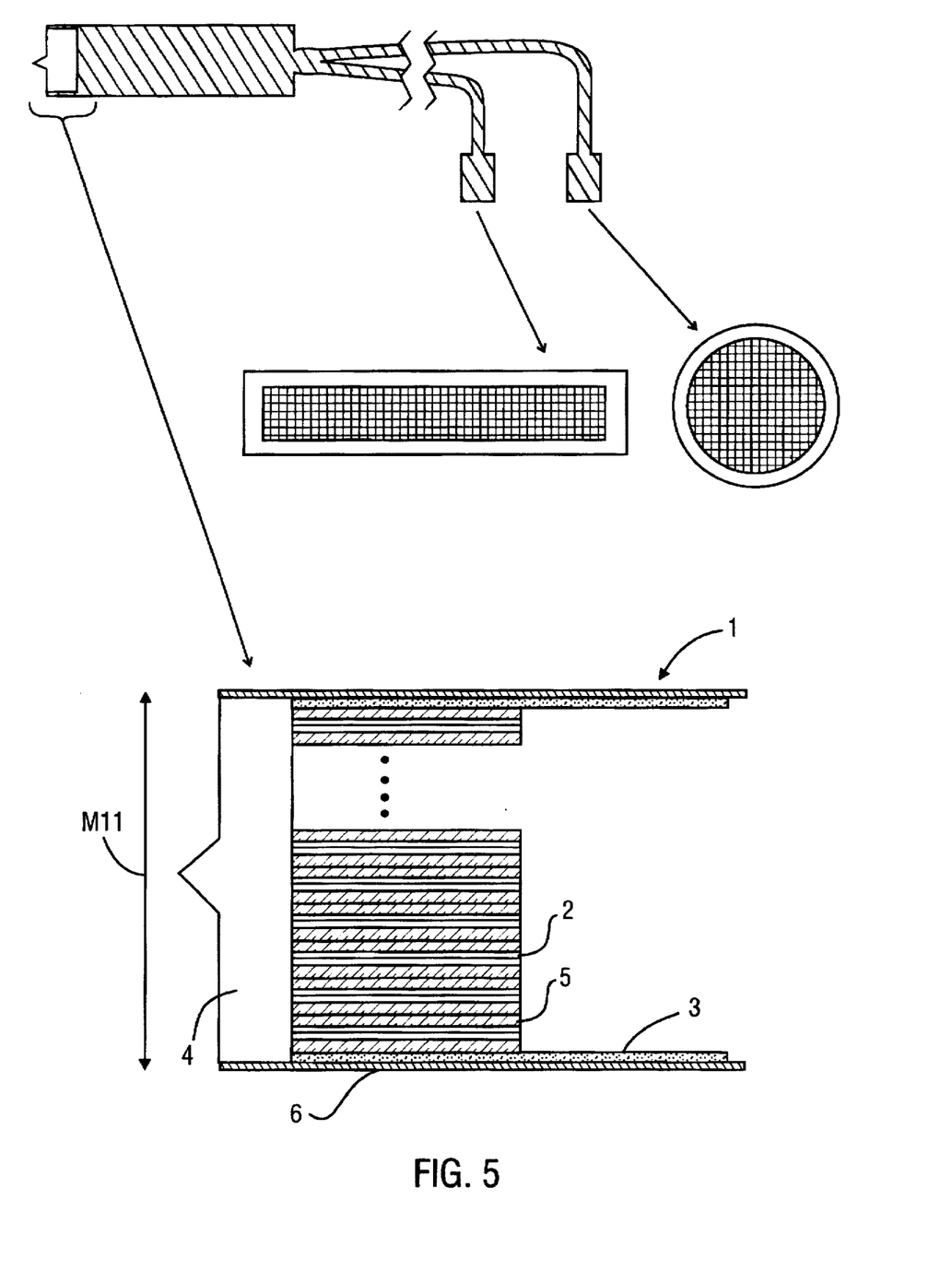
FIG. 5 shows a transverse section of a 40 mm probe tip, in accordance with an embodiment of the present invention.
Figure 6:
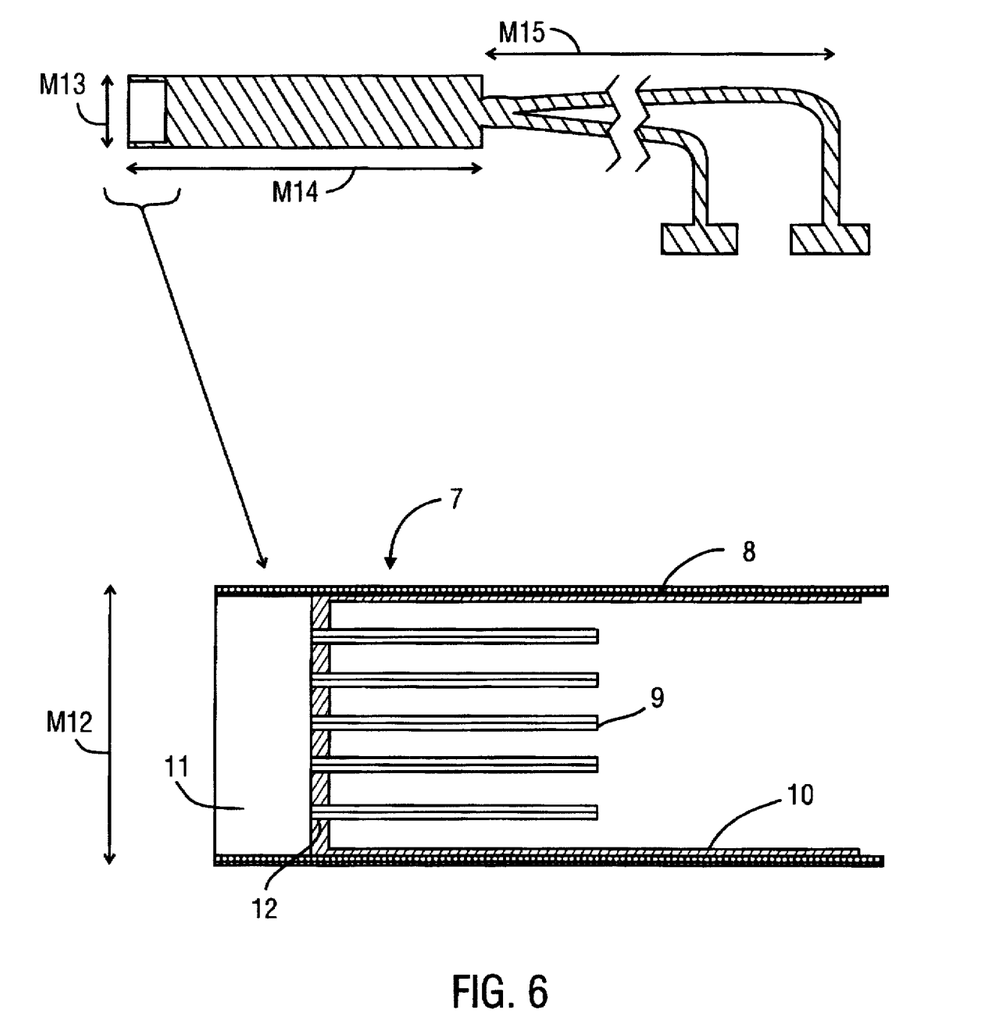
FIG. 6 shows a transverse section of a 10 mm probe tip, in accordance with another embodiment of the present invention.

In order to achieve the proper configuration, it may be desirable to employ a perforated plate, the perforations of which are used to physically fix fiber pairs. The plate would be located at the second opening and secured by any available means to the housing. Alternatively, the fiber pairs may be encased in glass tubes that, when packed together, provide the appropriate spacing and arrangement. Tip configurations are illustrated in FIGS. 5 and 6.

The second opening is covered by a substantially optically transparent window. Materials used for the window may include quartz, glass, fused silica, sapphire or other suitable substantially optically transparent material. Preferred materials are quartz and BK7 glass. In one embodiment of the present invention, the window surface is shaped to conform with the sample surface, for example, the cervix. Because the cervix has an involuted structure, its desirable that the window surface be evoluted, i.e., the inverse or mirror of the cervix. While the precise structure of the window may vary somewhat, it generally will be conical in shape. In this way, the gap between the window surface and the sample across the probe tip will substantially be negated. Depending on the size of the probe tip, only a portion of the window may be conical in shape, the remainder being flat or having a curve that conforms to the area about the cervical opening.

Figure 3:
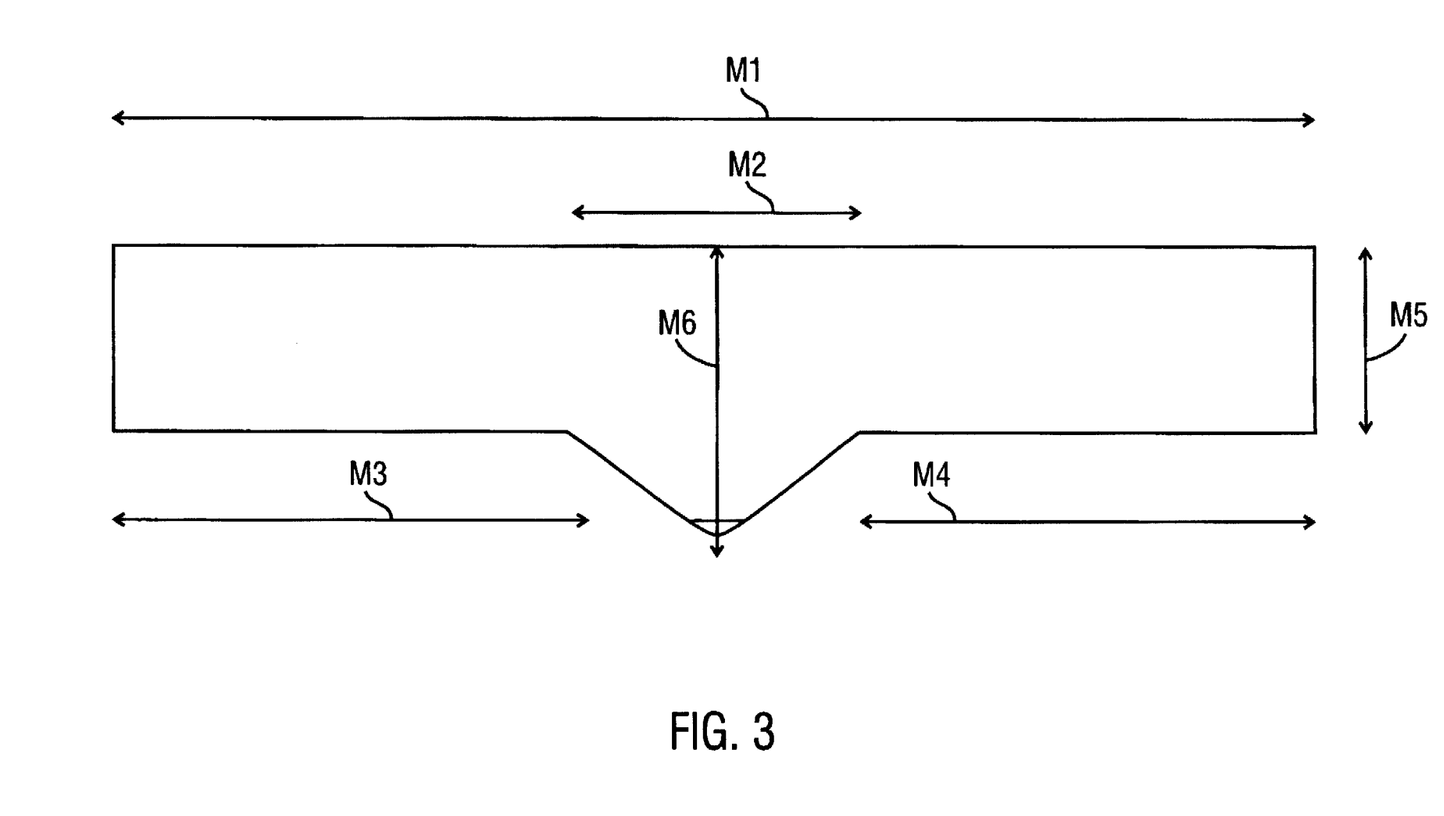
FIG. 3 shows a cross-section of a 42 mm window, in accordance with an embodiment of the present invention.
Figure 4A:
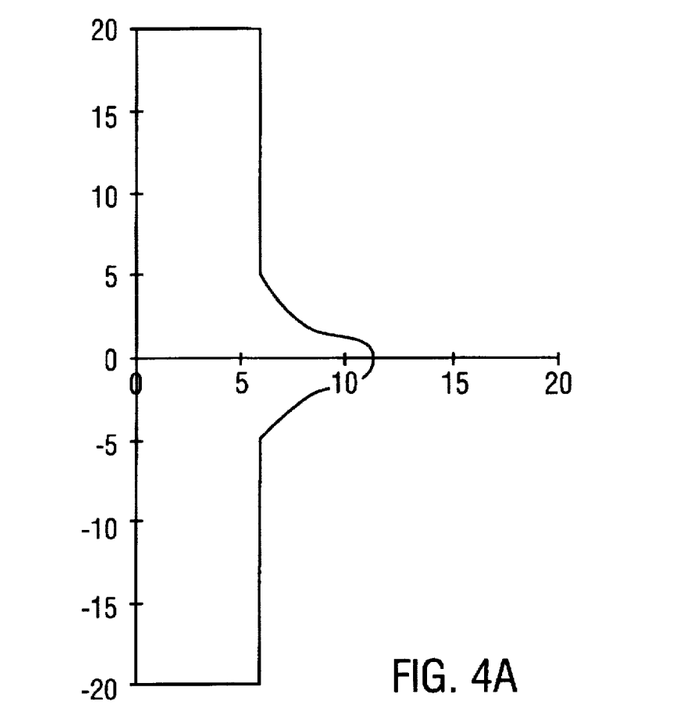
FIG. 4A shows a cross-section of a 40 mm window, in accordance with another embodiment of the present invention.
Figure 4B:
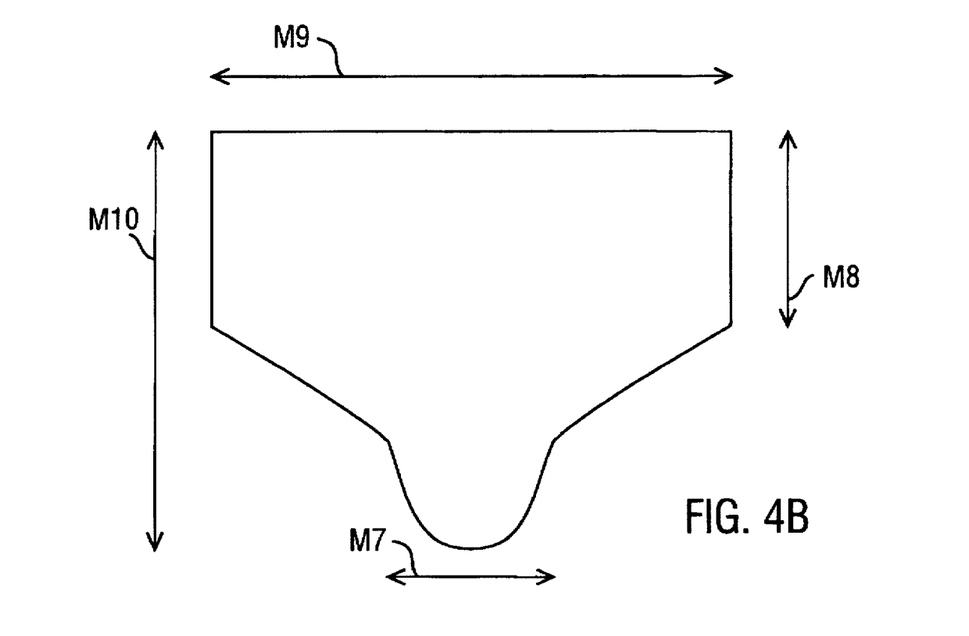
FIG. 4B shows a cross-section of a 10 mm window, in accordance with yet another embodiment of the present invention.

The window width and thickness will vary widely depending on the sample target. In general, for cervical probes, the window will range from about 10 mm to about 40 mm in width and the thickness will range from about 4 mm to about 10 mm. Examples are shown in FIGS. 3 and 4A and B.

B. Apparatus for Determining Fluorescent Spectra

Figure 7:
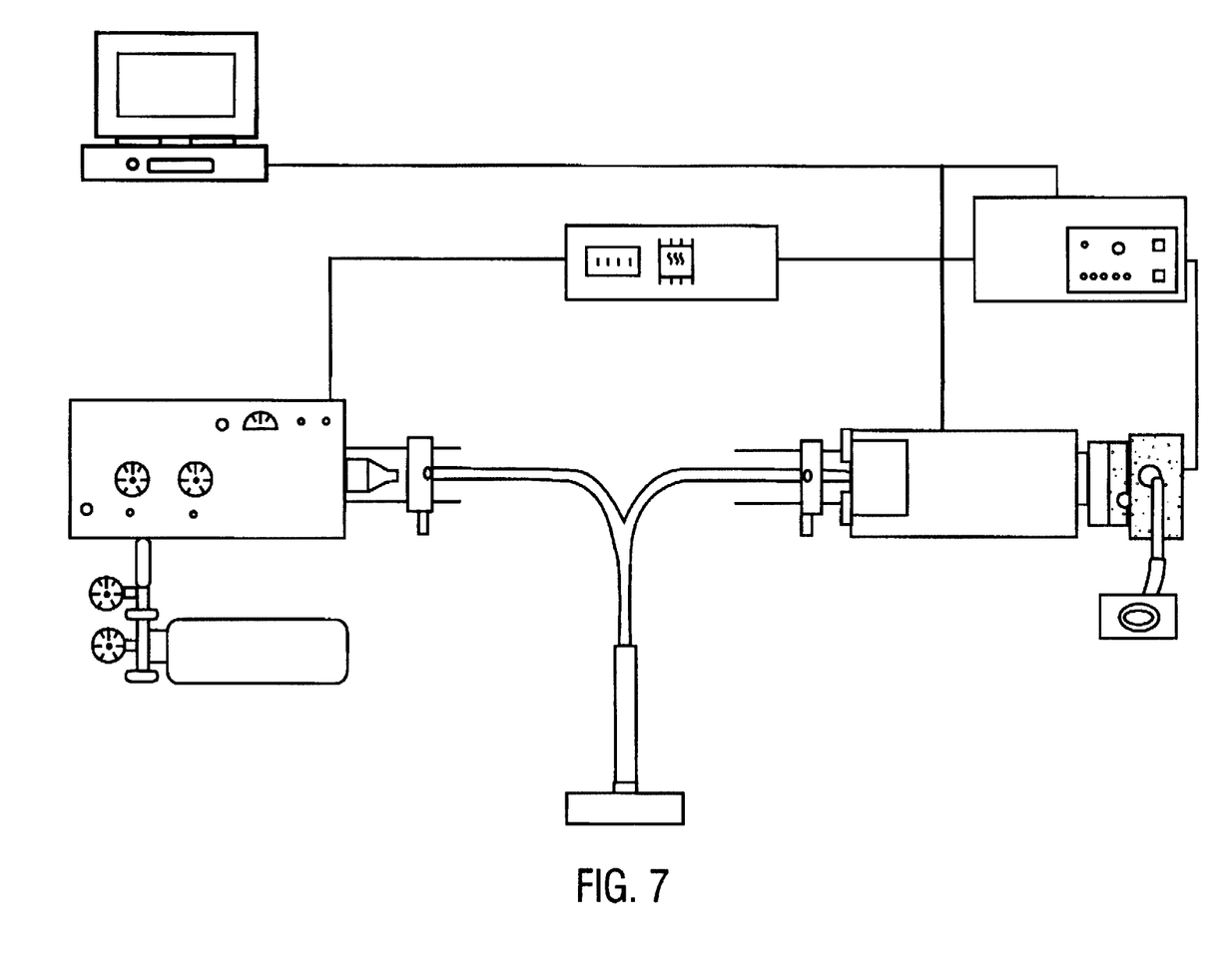
FIG. 7 is a diagram of an exemplary fluorescence spectroscopy diagnostic apparatus, incorporating the probe of the present invention.

The probe of the present invention is used as part of an apparatus for measuring tissue fluorescence. The apparatus comprises a probe, an electromagnetic radiation generator, a fluorescent spectrum detector and a means for analyzing the spectra in relation to said electromagnetic radiation. Typically, the means for analyzing the spectra will be a computer equipped with the proper interpretive software, which can be selected by those of skill in the art depending on the particular purpose to which it is applied. FIG. 7 is an exemplary spectroscopic system for collecting and analyzing fluorescence spectra from tissue samples, in accordance with the present invention.

Figure 8:
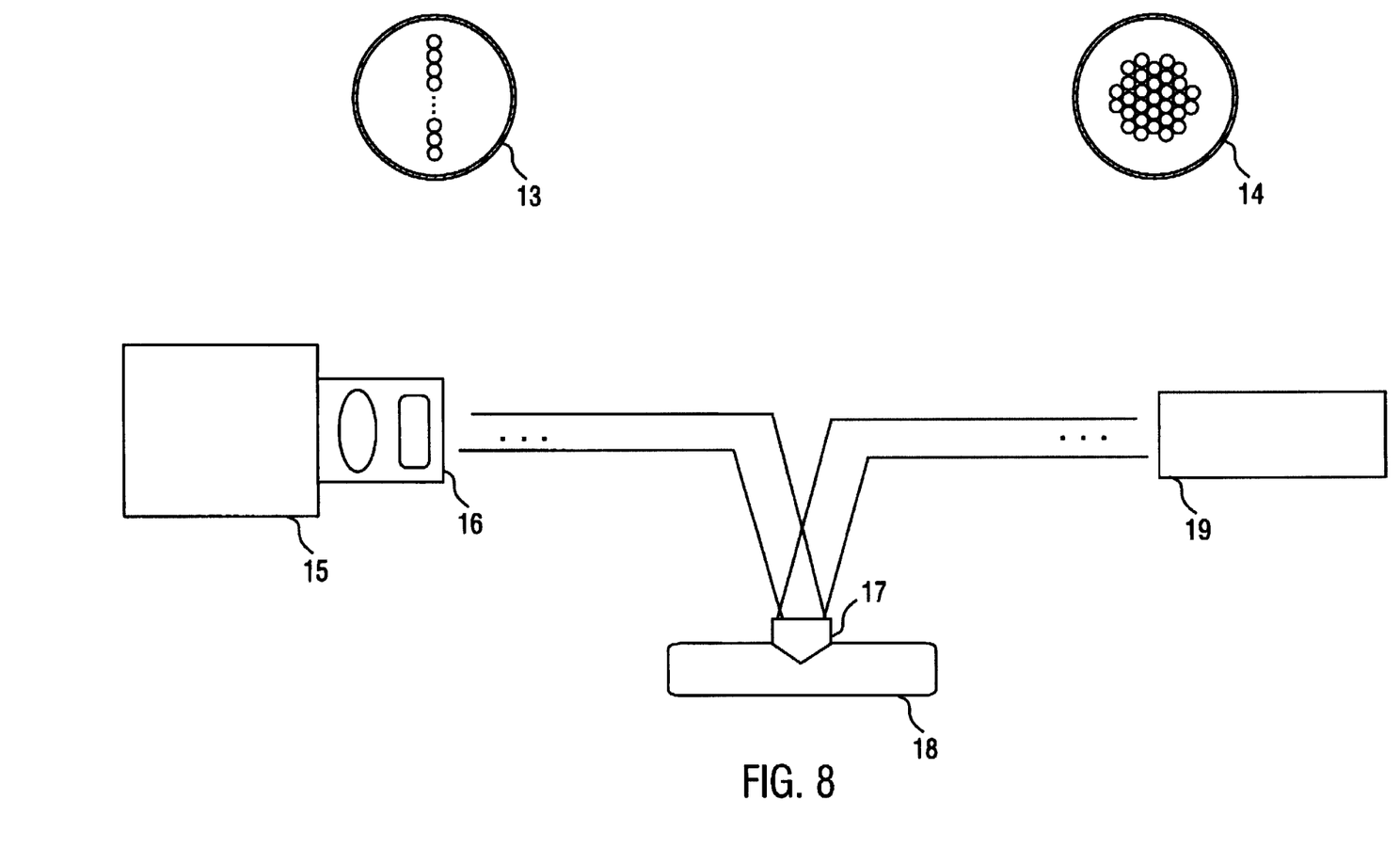
FIG. 8 illustrates fiber arrangement by couplers at the excitation and collection ends of the probe of the present invention.

An important part of the apparatus is means by which the fiber pairs are connected to the electromagnetic radiation generator and the fluorescent spectrum detector. These coupling means arrange the fiber pairs into a particular cross-section. For the coupling means attaching the fiber pairs to the electromagnetic radiation generator, the fiber pairs may be arranged in any fashion but typically, to save space, the fibers are packed as a bundle. The coupling means for the fluorescent spectra detector preferably arrange the fiber pairs in a linear fashion. This is needed because fluorescent spectra detectors often have a linear (vertical) aperture through which light samples are fed. See FIG. 8.

APPENDIX I: REFERENCES

The disclosures of the following publications, patents and applications are expressly incorporated herein by reference, as are any of the other references mentioned above:

A two-stage fluorescence diagnostic method is disclosed in detail in application Ser. No. 08/060,432, filed May 12, 1993, and is assigned to the same assignee as the present invention.

A patent, U.S. Pat. No. 5,125,404, entitled "Apparatus and Method for Obtaining Spectrally Resolved Spatial Images of Tissue" (Kittrell et al.) was filed on Nov. 21, 1989.

An application entitled "Optical Method And apparatus for the Diagnosis of Cervical Precancers using Raman and Fluorescence Spectroscopies" (Richards-Kortum et al.) was filed on Mar. 14, 1995, and is assigned to the same assignee as the present invention.

Lui et al.,"Fluorescence and Time-Resolved Light Scattering as Optical Diagnostic Techniques to Separate Diseased and Normal Biomedical Media," *J Photochem Photobiol B: Biol* 16, 187–209, 1992.

Wong et al., "Infrared Spectroscopy of Human Cervical Cells: Evidence of Extensive Structural Changes during Carcinogenesis", *Proc Nat'l Acad Sci USA*, 88, 10988–10992, 1991.

Kurman R. J., Henson D. E., Herbst A. L., Noller K. L., Shiffman M. H., "Interim guidelines for management of abnormal cervical cytology," *JAMA*, 271, 1866–1869, 1994.

Davison J. M., Marty J. J., "Detecting premalignant cervical lesions: Contributions of screening colposcopy to cytology," *J Reproductive Medicine*, 39, 388–392, 1994.

Banda-Gamboa, Hugo, et al, "Automation in cervical cytology: an overview," *Anal Cell Path*, 4 (1992) 25–48.

Chance B, Thorell L, "Localization and kinetics of reduced PN in living cells by microfluorimetry," *J Biol Chem* 234:3044, 1959.

Caspersson T. C., *Cell Structure and Function*, ch 4, Norton & Co, New York, 1950.

Aubin J. E., "Autofluorescence of Viable Cultured Mammalian Cells," *J Histochem Cytochem*, 27(1), 36–43, 1979.

Benson R. C., et al, "Cellular Autofluorescence: Is It Due to Flavins?" *J Histochem Cytochem*, 27(1), 44–48, 1979.

Tamura M., . . . Chance B., "In Vivo Study of Tissue Oxygen . . . ," *Annu Rev Physiol*, 1989 51:813–814.

Hutchinson, M. L., Agarwal, P., Denault, T., Berger, B., Cibas, ES, "A New Look at Cervical Cytology," *Acta Cytologica*, 36, 499–504, 1992.

Taylor D. G., Demas J. N., "Light intensity measurements I: Large area bolometers with uW sensitivities and absolute calibration of the rhodamine B quantum counter," *Anal Chem*, 51, 712–717, 1979.

Vooijs G. P., "Benign proliferative reactions, intraepithelial neoplasia and invasive cancer of the uterine cervix," in Bibbo M. (ed), *Comprehensive Cytopathology*, WB Saunders Company, pp 176–177, 1991.

Dillon W. R. and Goldstein M., "Multivariate Analysis Methods and Applications," Chapter 10. Wiley & Sons, New York (1985)

What is claimed is:

1. An optical probe for cervical examination comprising:
    (a) a probe casing having an elongate portion and at least two openings, wherein one of said openings is disposed at a distal tip of said elongate portion of said casing;
    (b) a plurality of optical fiber pairs, each of said pairs comprising an excitation fiber and a collection fiber, said optical fibers entering said casing at the non-tip opening and traversing said casing to said tip opening; and
    (c) a substantially optically transparent window with a surface structured to conform to the surface of the human cervix, said window covering said tip opening.

2. The probe according to claim 1, wherein at least a portion of said window is substantially conical.

3. The probe according to claim 2, wherein said window surface also comprises a non-conical portion.

4. The probe according to claim 3, wherein said tip is about 40 mm in width, having a minimum thickness of about 6.6 mm and a maximum thickness of about 10 mm, and said conical portion is about 10 mm in width.

5. The probe according to claim 5, wherein said probe casing is a hollow tube.

6. The probe according to claim 5, wherein said probe casing is comprised of carbonized epoxy.

7. The probe according to claim 5, wherein said probe casing is comprised of aluminum.

8. The probe according to claim 1, wherein said probe casing is further encased in heat-shrink tubing.

9. The probe according to claim 1, wherein individual fibers are comprised of a core and a cladding.

10. The probe according to claim 9, wherein said plurality is 31 or greater.

11. The probe according to claim 10, wherein said plurality is greater than 357 or greater.

12. The probe according to claim 1, wherein said window is comprised of quartz.

13. The probe according to claim 1, wherein said window is comprised of BK7 glass.

14. The probe according to claim 1, wherein said tip is about 10 mm in width, having a minimum thickness of about 4 mm and a maximum thickness of about 7.6 mm.

15. The probe according to claim 1, wherein said tip further comprises a perforated plate.

16. The probe according to claim 15, wherein said plate is aluminum and said perforations are 500 μm in diameter and spaced every 2 mm.

17. The probe according to claim 1, wherein each of said fiber pairs are disposed in the center of glass tubes, said glass tubes having an inner diameter of 500 μm and an outer diameter of 2 mm.

18. An apparatus for measuring tissue fluorescence comprising
    (a) a probe according to claim 1;
    (b) an electromagnetic radiation generator coupled to each excitation fiber;
    (c) a fluorescence spectrum detector coupled to each collection fiber; and
    (d) means coupled to the fluorescence spectrum detector for analyzing spectral information.

19. The apparatus of claim 18, wherein said fiber pairs of said probe are connected to said fluorescent spectrum detector by a coupling means, said fiber pairs in said coupling means being arranged in a substantially linear fashion.

20. A probe for the optical examination of a generally annular region of the human cervix comprising:
    (a) a generally elongated probe body having an optically transparent distal region generally in conformity with the generally annular cervix region;
    (b) an excitation fiber traversing at least a portion of the probe body to the distal region having an optical axis traverse to a portion of the distal region; and
    (c) a plurality of collection fibers traversing at least a portion of the probe body to the distal region and having respective optical axes transverse to portions of the distal region.

21. A probe as in claim 20, wherein the probe body further comprises a housing, the distal region comprising a generally planar section coupled to the housing and a generally conical section extending from the planar section.

* * * * *

UNITED STATES PATENT AND TRADEMARK OFFICE
CERTIFICATE OF CORRECTION

PATENT NO. : 5,699,795

DATED : December 23, 1997

INVENTOR(S) : Rebecca Richards-Kortum, Costas Pitris and Michele Follen Mitchell It is certified that error appears in the above-identified patent and that said Letters Patent is hereby corrected as shown below:

On the title page;
Under "References Cited", please add:

--U.S. PATENT DOCUMENTS
| | | | |
|---|---|---|---|
| 5,003,977 | 4/02/91 | Suzuki, *et al.* | 128/633 |
| 5,293,872 | 3/15/94 | Alfano, *et al.* | 128/664 |
| 5,348,003 | 9/20/94 | Caro | 128/633 |
| 5,450,847 | 9/19/95 | Garfield *et al.* | 128/778 |

FOREIGN PATENT DOCUMENTS
| | |
|---|---|
| EP 0 359 433 | 3/21/90 |
| EP 0 650 694 | 5/03/95 |
| WO 90/06718 | 6/28/90 |
| WO 90/12536 | 11/01/90 |
| WO 92/15008 | 9/03/92 |
| WO 93/03672 | 3/04/93 |
| WO 94/26168 | 11/24/94-- |

Signed and Sealed this

Seventh Day of April, 1998

*Attest:*

BRUCE LEHMAN

*Attesting Officer*      *Commissioner of Patents and Trademarks*